United States Patent
Stott et al.

(10) Patent No.: US 9,962,341 B2
(45) Date of Patent: May 8, 2018

(54) ACTIVE PHARMACEUTICAL INGREDIENT (API) COMPRISING CANNABINOIDS FOR USE IN THE TREATMENT OF CANCER

(71) Applicant: GW Pharma Limited, Histon, Cambridge, Cambridgeshire (GB)

(72) Inventors: Colin Stott, Histon (GB); Marnie Duncan, Histon (GB); Thomas Hill, Histon (GB)

(73) Assignee: GW Pharma Limited, Cambridge (GB)

( * ) Notice: Subject to any disclaimer, the term of this patent is extended or adjusted under 35 U.S.C. 154(b) by 0 days. days.

(21) Appl. No.: 15/321,766

(22) PCT Filed: Jun. 26, 2015

(86) PCT No.: PCT/GB2015/051876
§ 371 (c)(1),
(2) Date: Dec. 23, 2016

(87) PCT Pub. No.: WO2015/198071
PCT Pub. Date: Dec. 30, 2015

(65) Prior Publication Data
US 2017/0143642 A1 May 25, 2017

(30) Foreign Application Priority Data
Jun. 27, 2014 (GB) .................................. 1411465.6

(51) Int. Cl.
*A61K 31/05* (2006.01)
(52) U.S. Cl.
CPC .................................... *A61K 31/05* (2013.01)
(58) Field of Classification Search
None
See application file for complete search history.

(56) References Cited

FOREIGN PATENT DOCUMENTS

| EP | 1 802 274 A1 | 7/2007 |
|---|---|---|
| GB | 2 418 612 A | 4/2006 |
| GB | 2 494 461 A | 3/2013 |
| GB | 2 515 312 A | 12/2014 |
| WO | WO 2009/147438 A1 | 12/2009 |
| WO | WO 2009/147439 A1 | 12/2009 |
| WO | WO 2011/110866 A1 | 9/2011 |
| WO | WO 2013/038157 A1 | 3/2013 |
| WO | WO 2014/202990 A1 | 12/2014 |

OTHER PUBLICATIONS

Baek et al., Synthesis and antitumor activity of cannabigerol. Arch Pharm Res. Jun. 1996;19(3):228-30.
Choi et al., Cannabidiol induces cytotoxicity and cell death via apoptotic pathway in cancer cell lines. Biomolecules and Therapeutics. Jun. 2008;16(2):87-94.
Chou et al., Quantitative analysis of close-effect relationships: the combined effects of multiple drugs or enzyme inhibitors. Adv Enzyme Regul. 1984;22:27-55.
Chou, Theoretical basis, experimental design, and computerized simulation of synergism and antagonism in drug combination studies. Pharmacol Rev. Sep. 2006;58(3):621-81. Review. Erratum in: Pharmacol Rev. Mar. 2007;59(1):124.
Ligresti et al., Antitumor activity of plant cannabinoids with emphasis on the effect of cannabidiol on human breast carcinoma. J Pharmacol Exp Ther. Sep. 2006;318(3):1375-87. Epub May 25, 2006.
Massi et al., Antitumor effects of cannabidiol, a nonpsychoactive cannabinoid, on human glioma cell lines. J Pharmacol Exp Ther. Mar. 2004;308(3):838-45. Epub Nov. 14, 2003.
McAllister et al., Cannabidiol as a novel inhibitor of Id-1 gene expression in aggressive breast cancer cells. Mol Cancer Ther. Nov. 2007;6(11):2921-7.

*Primary Examiner* — Samantha L Shterengarts
(74) *Attorney, Agent, or Firm* — Wolf, Greenfield & Sacks, P.C.

(57) ABSTRACT

The present invention relates to an active pharmaceutical ingredient (API) which comprises or consists essentially of cannabidiol (CBD) and one other cannabinoid selected from cannabigerol (CBG), cannabigerolic acid (CBGA), cannabidiolic acid (CBDA), and tetrahydrocannabivarin (THCV) for use as a medicament, and more particularly, for use in the treatment of cancer. These combinations have shown themselves to be synergistic in treating one or more of: breast cancer; liver cancer; lung cancer; pancreatic cancer; melanoma; ovarian cancer; gastric cancer; renal cancer or bladder cancer. Two particularly favored API combinations are: cannabidiol (CBD) and cannabigerol (CBG); and cannabidiolic (CBD) and tetrahydrocannabivarin (THCV).

9 Claims, No Drawings

ACTIVE PHARMACEUTICAL INGREDIENT (API) COMPRISING CANNABINOIDS FOR USE IN THE TREATMENT OF CANCER

RELATED APPLICATION

This application is a national stage filing under 35 U.S.C. § 371 of International Application No. PCT/GB2015/051876, filed Jun. 26, 2015, which was published under PCT Article 21(2) in English, the entire contents of which are hereby incorporated by reference.

The present invention relates to an active pharmaceutical ingredient (API) which comprises or consists essentially of cannabidiol (CBD) and one other cannabinoid selected from cannabigerol (CBG), cannabigerolic acid (CBGA), cannabidiolic acid (CBDA), and tetrahydrocannabivarin (THCV) for use as a medicament, and more particularly, for use in the treatment of cancer.

These combinations have shown themselves to be synergistic in treating one or more of: breast cancer; liver cancer; lung cancer; pancreatic cancer; melanoma; ovarian cancer; gastric cancer; renal cancer or bladder cancer.

Two particularly favored API combinations are: cannabidiol (CBD) and cannabigerol (CBG); and cannabidiolic (CBD) and tetrahydrocannabivarin (THCV).

BACKGROUND TO THE INVENTION

Cancer is a class of diseases which occur because cells become immortalised; they fail to heed customary signals to turn off growth which is a normal function of remodelling in the body that requires cells to die on cue. Apoptosis, or programmed cell death, can become defective and when this happens malignant transformation can take place. The immortalised cells grow beyond their normal limits and invade adjacent tissues. The malignant cells may also metastasise and spread to other locations in the body via the bloodstream or lymphatic system. Cancer cells often form a mass known as a tumour.

There are about 200 different types of cancer; the cancers can start in any type of body tissue although many cancers will metastasise into other body tissues. There are many different causes of cancer and these include; carcinogens, age, genetic mutations, immune system problems, diet, weight, lifestyle, environmental factors such as pollutants, some viruses, for example, the human papilloma virus (HPV) is implicated in cervical cancer.

There are many different treatment options for cancer and the treatment sought is often determined by the type and stage of the cancer. Treatment options include; chemotherapeutic drug treatment, hormonal drug treatment, radiotherapy, surgery, complementary therapies and combinations thereof.

*Cannabis* has been ascribed to be both a carcinogen and anti-cancer agent. In particular smoking *cannabis* is known to be carcinogenic as the *cannabis* smoke contains at least 50 different known carcinogenic compounds, many of which are the same substances found in smoked tobacco. One of these carcinogens, benzopyrene is known to cause cancer as it alters a gene called p53, which is a tumour suppressor gene.

Researchers have discovered that some cannabinoids, including tetrahydrocannabinol (THC) and cannabidiol (CBD) are able to promote the re-emergence of apoptosis so that some tumours will heed the signals, stop dividing, and die. The process of apoptosis is judged by observation of several phenomena including: reduced cellular volume, condensation of nuclear chromatin, changes in distribution of phospholipids in plasma membrane phospholipids, and cleavage of chromatin into DNA fragments called DNA ladders.

Another method by which tumours grow is by ensuring that they are nourished: they send out signals to promote angiogenesis, the growth of new blood vessels. Cannabinoids may turn off these signals as well.

Cannabinoids have been shown to have an anti-proliferative effect on different cancer cell lines. The cannabinoids THC, tetrahydrocannabinol acid (THCA), CBD, cannabidiolic acid (CBDA), cannabigerol (CBG) and cannabichromene (CBC) and the cannabinoid extracts enriched in either THC or CBD were tested on eight different cell lines in Ligresti et al., (2006). The lines used in this study were: DU-145 (hormone-insensitive prostate cancer), MDA-MB-231 and MCF-7 (breast cancer), CaCo-2 (colorectal cancer), LiMol (thyroid cancer), RBL-2H3 (leukaemia), AGS (gastric cancer) and C6 (glioma cells).

The data for each cannabinoid in each different type of cancer varied but generally the best data were observed with CBD or the *cannabis* extract enriched in CBD.

The IC50 values varied widely between the different cannabinoids and the different cell lines; however the authors determined that the cannabinoid CBD was the most effective in the breast cancer cell lines.

Several patent applications describe the use of cannabinoids in the treatment of brain tumours, for example WO 2009/147439 describes a combination of THC and CBD in the treatment of glioma, WO 2009/147438 describes the use of THC and CBD in combination with non-cannabinoid chemotherapeutic agents in the treatment of glioma and WO 2011/110866 describes the use of THC and CBD with temozolamide in the treatment of glioma.

The patent EP1,802,274 describes the use of the cannabinoid CBD in the inhibition of tumour cell migration.

A later study ascribed a mechanism to this, by demonstrating that CBD is able to able to down-regulate the expression of the DNA binding protein inhibitor, Id-1 in human breast cancer cells (McAllister, 2007). The CBD concentrations effective at inhibiting Id-1 expression correlated with those used to inhibit the proliferative and invasive phenotype of breast cancer cells. CBD was able to inhibit Id-1 expression at the mRNA and protein level in a concentration-dependent fashion.

CBD has also been shown to inhibit human cancer cell proliferation and invasion through differential modulation of the ERK and ROS pathways, and that sustained activation of the ERK pathway leads to down-regulation of Id-1 expression. It was also demonstrated that CBD up-regulates the pro-differentiation agent, Id-2. Using a mouse 4T1 cell line and a model of metastatic breast cancer, CBD significantly reduced metastatic spread. As such CBD may represent a promising treatment of breast cancer in patients with secondary tumours (McAllister, 2007).

The patent application GB2494461 describes the use of the cannabinoids CBG, CBDV and THCV in the treatment of U87 glioma cells.

Choi et al. (2008) describes the efficacy of CBD in a number of cell lines and that the cytotoxicity of CBD increased in a dose and time dependant manner. Furthermore Baek et al. (1996) suggests that CBG exerts an anti-tumour activity against melanoma cells in a mouse model.

It is an object of the present invention to find improved and/or alternative cancer therapies. To this end a platform of data representing the use of an API comprising or consisting essentially of a combination of cannabidiol with another cannabinoid selected from cannabigerol (CBG), cannabigerolic acid (CBGA), cannabidiolic acid (CBDA), and tetrahydrocannabivarin (THCV) in various cancer cell lines.

DEFINITIONS AND ABBREVIATIONS

Definitions of some of the terms used to describe the invention are detailed below:

The phytocannabinoids described in the present application are listed below along with their standard abbreviations.

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phyto- CBD    Cannabidiol

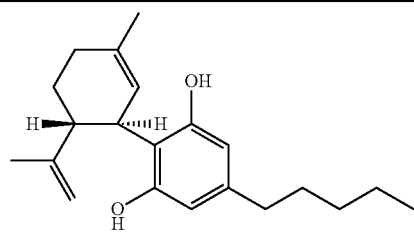

CBDA   Cannabidiolic acid

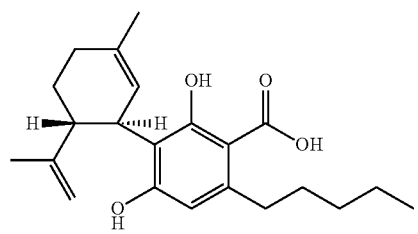 [SMILES: C=C(C)[C@@H]1CCC(C)=C[C@H]1c1c(O)cc(CCCCC)c(C(=O)O)c1O]

CBG    Cannabigerol

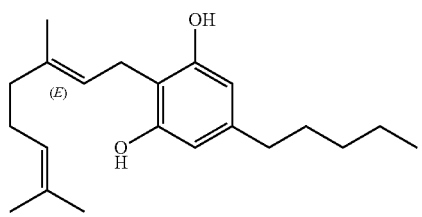 [SMILES: CCCCCc1cc(O)c(C/C=C(\C)CCC=C(C)C)c(O)c1]

CBGA   Cannabigerolic acid

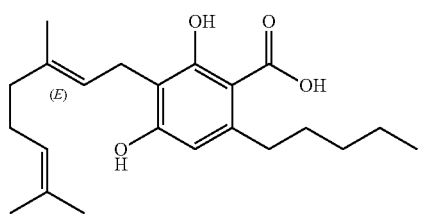 [SMILES: CCCCCc1cc(O)c(C/C=C(\C)CCC=C(C)C)c(O)c1C(=O)O]

THC    Tetrahydrocannabinol

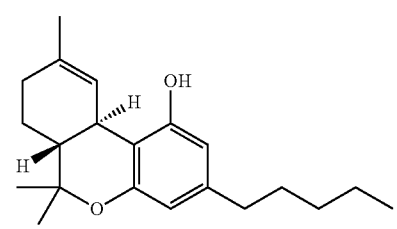 [SMILES: CCCCCc1cc(O)c2c(c1)OC(C)(C)[C@@H]1CCC(C)=C[C@@H]21]

THCV   Tetrahydrocannabivarin

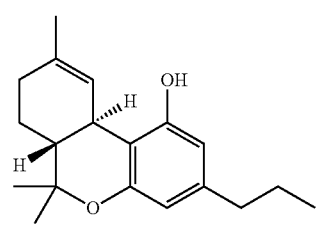 [SMILES: CCCc1cc(O)c2c(c1)OC(C)(C)[C@@H]1CCC(C)=C[C@@H]21]

cannabinoids can be isolated from plants to produce a highly purified extract or can be reproduced synthetically.

"Highly purified cannabinoids" are defined as cannabinoids that have been extracted from the *cannabis* plant and purified to the extent that other (non-required) cannabinoids and non-cannabinoid components that are co-extracted with the cannabinoids have been removed, such that the highly purified cannabinoid or cannabinoids is/are greater than or equal to 98% (w/w) pure. In the case of an API comprising a combination of two cannabinoids the two comprise greater than or equal to 98% (w/w) of the total weight.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Active Pharmaceutical Ingredient" (API) is defined by the FDA as "any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body." As such a synergistic combination falls under the definition of an API.

The term "comprising" refers to the specified cannabinoids being present in the API at greater than 95% (w/w).

The term "consisting essentially of" refers to the specified cannabinoids being present in the API at greater than 98% (w/w).

BRIEF SUMMARY OF THE DISCLOSURE

In accordance with a first aspect of the present invention there is provided an active pharmaceutical ingredient (API) comprising or consisting essentially of cannabidiol (CBD) and another cannabinoid (CB) selected from the group consisting of cannabigerol (CBG), cannabigerolic acid (CBGA), cannabidiolic acid (CBDA) and tetrahydrocannabivarin (THCV) for use as a medicament.

In one embodiment the API comprises or consists essentially of cannabidiol (CBD) and cannabigerol (CBG).

In a second embodiment the API comprises or consists essentially of cannabidiol (CBD) and cannabigerolic acid (CBGA).

In a third embodiment the API comprises or consists essentially of cannabidiol (CBD) and cannabidiolic acid (CBDA) for use as a medicament.

In a fourth embodiment the API comprises or consists essentially of cannabidiol (CBD) and tetrahydrocannabivarin (THCV) for use as a medicament.

Preferably the API is for use in the treatment of cancer.

More preferably the cancer is one or more of: breast cancer; liver cancer; lung cancer; pancreatic cancer; melanoma; ovarian cancer; gastric cancer; renal cancer or bladder cancer.

Preferably the CBD and another cannabinoid are present in a ratio of from 7.5:1 to 1:7.5 (CBD:CB); through 7.5:1 to 2.5:1 (CBD:CB); through 5:1 to 2.5:1 (CBD:CB); through 2:1 to 1:2 (CBD:CB) to a ratio of 1:1 (CBD:CB).

In a further embodiment the cancer is breast cancer and the API is selected from the group consisting of CBD and CBG, CBD and CBDA, CBD and THCV, and CBD and CBGA.

In a further embodiment the cancer is lung cancer and the API is selected from the group consisting of CBD and CBG, CBD and CBDA, CBD and THCV, and CBD and CBGA.

In a further embodiment the cancer is pancreatic cancer and the API is selected from the group consisting of CBD and CBG, and CBD and THCV.

In a further embodiment the cancer is melanoma and the API is selected from the group consisting of CBD and CBG, and CBD and THCV.

In a further embodiment the cancer is ovarian cancer and the API is selected from the group consisting of CBD and CBG, CBD and CBDA, CBD and THCV, and CBD and CBGA.

In a further embodiment the cancer is gastric cancer and the API is selected from the group consisting of CBD and CBG, and CBD and THCV.

In a further embodiment the cancer is renal cancer and the API is CBD and THCV.

In a further embodiment still the cancer is bladder cancer and the API is selected from the group consisting of CBD and CBG.

Preferably the dose of API is between 1 and 1000 mg/kg day.

In a further embodiment there is provided a pharmaceutical formulation comprising an API and one or more excipients.

Preferably the pharmaceutical formulation comprises CBD is in combination with another cannabinoid (CB) selected from the group consisting of cannabigerol (CBG), cannabigerolic acid (CBGA), cannabidiolic acid (CBDA) and tetrahydrocannabivarin (THCV) wherein the CBD may be formulated for administration separately, sequentially or simultaneously with the other CB or the combination may be provided in a single dosage form.

In accordance with a second aspect of the present invention there is provided a method of treating breast cancer; liver cancer; lung cancer; pancreatic cancer; melanoma; ovarian cancer; gastric cancer; renal cancer or bladder cancer, comprising administering an API comprising or consisting essentially of cannabidiol (CBD) and another cannabinoid selected from the group consisting of cannabigerol (CBG); cannabigerolic acid (CBGA); cannabidiolic acid (CBDA); and tetrahydrocannabivarin (THCV) to a patient in need thereof.

DETAILED DESCRIPTION

The Examples below describe for the first time various different active pharmaceutical ingredients (API) comprising combinations of cannabidiol and another cannabinoid (CB) selected from the group consisting of cannabigerol (CBG), cannabigerolic acid (CBGA), cannabidiolic acid (CBDA), and tetrahydrocannabivarin (THCV). These API are shown not only to be efficacious, but also the combinations show synergism in the treatment of many different cancer cell lines.

EXAMPLE 1

Efficacy of Phytocannabinoids Alone and in Combination in Breast and Liver Cancer Cell Lines Materials and Methods Cell Lines:

The cell lines tested in this Example were as follows. Breast cancer: MDA-MB-231; SK-BR3; and BT474. Liver cancer: HepG2.

The phytocannabinoids were tested alone and in various ratioed combinations in media containing final concentrations of 10% and 1% foetal bovine serum at 72 h for the breast and prostate cancer lines and 1% foetal bovine serum for the liver cancer line HepG2.

Cell Preparation:

Each tumour cell line was maintained in vitro in RPMI 1640+10% heat inactivated FBS and 2 mM L-glutamine (growth media) at 37° C. in 5% CO2 and humidified conditions. The cells were harvested, washed, re-suspended into growth medium and counted. The cells were re-suspended into assay media (RPMI 1640+5% heat inactivated FBS+ and 2 mM L-glutamine) at $8\times10^4$-$2\times10^5$ cells/ml (dependent upon cell type) and plated into the middle 240 wells of 384 well tissue culture plates (Corning CellBind, black-wall plates) 12.5 μl/well aliquots; 62.5 μl of growth media was aliquoted into the outer wells. There were 4 plates for each cell line. The plates were incubated overnight at 37° C., in 5% humidified $CO_2$.

Phytocannabinoid Preparation and Plating (1% FBS):

The phytocannabinoid test compounds were prepared in 100% DMSO vehicle at a stock concentration of 10 mM.

Dilution of Single Phytocannabinoid Compound on its Own:

Starting with the 10 mM stock, the compounds were diluted to 125 μM in FBS-free growth media.

Combination of Phytocannabinoids in a 1:1 Ratio:

Equal volumes of 10 mM stocks were mixed together to give final concentration of 5 mM of each compound. These were diluted in FBS-free growth media to 125 μM before serial dilution.

Combination of Phytocannabinoids in a 5:1 Ratio:

5 volumes of CBD 10 mM stock was added to 1 volume of the other agent (also at 10 mM) and 4 volumes of DMSO. This made a final concentration of 5 mM:1 mM. This was then diluted in FBS-free growth media so the top concentration of CBD would be 125 μM (before serial dilution). Each compound and compound combination stock was serially diluted in FBS-free growth media (containing 1.25% v/v DMSO) from 125 μM to 41.7, 13.89, 4.63, 1.54, 0.514, 0.171, 0.057 and 0.019 μM (1.25× final assay concentrations). Vehicle was prepared at equivalent dilutions in assay media. The top final concentration of compound in the assay was always 100 μM so CBD5:1CBG was 100 μM CBD and 20 μM CBG.

Positive Controls:

Taxotere SOC was prepared at a stock concentration of 1 mM in 100% DMSO. Taxotere was serially diluted from the stock solution into FBS-free growth media to 12.5 μM, then serially diluted in FBS-free growth media containing 1.25% DMSO to 4.17, 1.39, 0.46, 0.154, 0.051, 0.017, 0.006, 0.002 μM (1.25× final assay concentrations).

Herceptin (in the clinical formulation) was diluted in FBS-free media and then diluted in FBS-free media to 1.25 μM. This was then serially diluted in FBS-free growth media to 0.417, 0.139, 0.046, 0.0154, 0.0051, 0.0017, 0.0006, 0.0002 μM (1.25× final assay concentrations). This was plated as a positive control for the SKBR3 & BT474 cell lines. 50 μl per well of compound/vehicle dilutions was added to the plates in replicates of 6. Where applicable total volume in the well was made up to 62.5 μl with assay media.

Assay Conditions:

The plates were incubated for 72 h at 37° C. in 5% humidified $CO_2$. To develop the plates, at 72 h, 10 μl of CellTiter-Blue™ reagent was added to each test/blank well. The plates were incubated at 37° C., 5% humidified $CO_2$. Fluorescence was measured using a Flex II Station plate reader (570 nm excitation wavelength, 600 nm emission wavelength, 590 nm cut-off) after 3 h.

Experiment with 10% FBS Final Concentration:

The experimental conditions were the same as the experiment above, with the same compound dilutions and volumes for plating but using growth media containing 10% FBS rather than FBS-free media.

Results

The phytocannabinoids were tested alone and in combination with CBD on a panel of breast (BT474, MDA-MB231, SKBR3), and liver (HepG2) cancer lines. The IC50 value for each phytocannabinoid was calculated both alone and in combination in each cell line.

The raw data values expressed in relative fluorescent units were normalised to the vehicle for each individual plate and any reduction in fluorescence indicated a decrease in viability.

The data were analysed in GraphPad PRISM using a non-linear sigmoidal plot with variable slope (asymmetric five point linear regression) and where possible an IC50 value for each single compound and combination was generated. Using this analysis, where the IC50 95% confidence intervals (automatically generated in GraphPad PRISM) for CDB alone and in combination did not overlap, this was graded as significant (p<0.05).

The IC50 values calculated are summarised in Tables 1 and 2 below.

TABLE 1

IC50 values of phytocannabinoids and combinations in cell lines in the presence of 1% FBS

| Phytocannabinoid | Breast | | | Liver |
| | BT474 | MDA-MB-231 | SKBR3 | HepG2 |
| --- | --- | --- | --- | --- |
| CBD | 8.0 | 7.4 | 4.0 | 3.3 |
| CBG | 7.9 | 4.1 | 4.0 | 3.7 |
| CBGA | 24.8 | 16 | 10.6 | 9.3 |
| CBDA | 21.8 | 30 | 14.5 | 7.4 |
| THCV | 13.3 | 14.4 | 10.8 | 7.2 |
| CBD1:CBG1 | 3.7* | 3.7 | 3.5 | 1.6* |
| CBD1:CBGA1 | 8.4 | 10.8 | 9.6 | 3.4 |
| CBD1:CBDA1 | 7.9 | 9.8 | 3.8 | 4.0* |
| CBD1:THCV1 | 4.2* | 4.4 | 3.1 | 2.9* |
| CBD5:CBG1 | 8.8 | 9.7 | 3.6 | 3.8 |
| CBD5:CBGA1 | 8.8 | 8.0 | 3.6 | 3.9 |
| CBD5:CBDA1 | 12.8 | 10.5 | 3.7 | 4.4* |
| CBD5:THCV1 | 7.9 | 5.1 | 6.0 | 3.8* |
| Taxotere | <1 nM (but only 50% effect) | <1 nM (but only 50% effect) | <1 nM (but only 50% effect) | |
| Herceptin | 1.7 | NT | >1.0 | NT |

*= significantly different (p = <0.05) from CBD on its own
NT = Not tested

TABLE 2

IC50 values of phytocannabinoids and combinations
in cell lines in the presence of 10% FBS

| | Breast | | |
|---|---|---|---|
| Phytocannabinoid | BT474 | MDA-MB-231 | SKBR3 |
| CBD | 28 | 27 | 23 |
| CBG | 37 | 29 | 33 |
| CBGA | ~100 | ~100 | >100 |
| CBDA | >100 | NE at 100 μM | ~100 |
| THCV | 31 | 36 | 30 |
| CBD1:CBG1 | 13 | 12 | 3* |
| CBD1:CBGA1 | 32 | 27 | 15 |
| CBD1:CBDA1 | 26 | 27 | 25 |
| CBD1:THCV1 | 3 | 26 | 13 |
| CBD5:CBG1 | 28 | 28 | 17 |
| CBD5:CBGA1 | 27 | 20 | 23 |
| CBD5:CBDA1 | 36 | 14 | 29 |
| CBD5:THCV1 | 26 | 19 | 20 |
| Taxotere | <1 nM (but only 50% effect) | <1 nM (but only 50% effect) | <1 nM (but only 50% effect) |
| Herceptin | 13 nM | NT | NE at 1 μM |

\*= significantly different (p = <0.05) from CBD only
NT = Not tested
NE = No effect
~= Not able to determine accurate IC50

The IC50 values of the phytocannabinoid agents on their own and in combination were lower in cells tested in media containing 1% FBS compared to 10%. This is likely to be due to the fact that these compounds are highly bound to plasma proteins and so in media containing 10% FBS, less compound is available to the cells to have an effect.

In general CBD and CBG on their own were more potent than the acid variants CBGA and CBDA across the cell lines tested.

THCV was also generally more potent than CBGA and CBDA. Each single p had a similar IC50 value against each of the five cell lines tested with no more than a 3-fold variation when tested.

The only exception to this was THCV which was measured as 5-fold more potent in LNCAP cells compared to DU145 cells in media containing 10% FBS.

When CBD was tested in combination with CBG and THCV at a 1:1 ratio in the BT474 cells in media containing 1% FBS there was significant decrease in IC50 value (p<0.05) compared to CBD treatment alone.

When CBD was tested in combination with CBG and THCV at a 1:1 ratio in the HepG2 cells there was a significant decrease in IC50 value (p<0.05) compared to CBD treatment alone. There was also a significant increase in IC50 value (p<0.05) when CBD was tested in a 1:1 combination with CBDA compared to CBD treatment alone.

When CBD was tested in the HepG2 (liver cancer) cells in combination with phytocannabinoids at a 5:1 ratio there was significant difference in the IC50 value (p<0.05) of the CBDA and THCV combinations compared to CBD treatment alone.

There was a significant decrease in IC50 value (p<0.05) when CBD was tested in combination with CBG in SKBR3 cells in media containing 10% FBS.

There was a general trend across all cell lines tested that the IC50 values of the 1:1 CBD combinations with CBG and THCV were lower than the IC50 value of CBD alone in the same cell line.

Generation of Combination Index (CI) Values of CBD in Combination with Other Phytocannabinoids Using the Chou-Talalay Method For the calculation, raw data values expressed in relative fluorescent units were normalised to the vehicle for each individual plate (set as 0%) and the reduction in fluorescence calculated as an increase in inhibition of viability.

The data was formatted in Excel for each assay plate so that the average effect at each concentration for each separate phytocannabinoid and each of the combinations could be determined.

The mean data at each concentration of CBD was imported into the analysis package Calcusyn. Calcusyn software was designed by M. Hayball and C. W. Lamble and calculates the combination index (CI) values based on the Chou and Talalay formula (Chou and Talalay, 1984). Using Calcusyn, the CI value of each of the combinations of CBD for each cell line was determined at the Effective Dose values of CBD at 50, 75, 90 and 95%. These are summarised on Tables 4 to 13. Also calculated was the weighted Combination Index (CIwt) calculated using the equation CIwt= (CI50+2CI75+3CI90+4CI95)/10 (Chou, 2006).

Table 3 contains the descriptive summaries of various CI values based according to Chou and also contains a glossary of terms of the data reported in subsequent tables.

TABLE 3

Verbal Descriptions of Synergism and Antagonism and Meaning of Terms used in tables 4 to 13

| CI | Description | Term | Explanation |
|---|---|---|---|
| <0.1 | Very Strong Synergism | CI | Combination Index |
| 0.1-0.30 | Strong Synergism | ED50 | Effective dose of Debio0932 giving 50% inhibition |
| 0.31-0.7 | Synergism | ED75 | Effective dose of Debio0932 giving 75% inhibition |
| 0.71-0.85 | Moderate Synergism | ED90 | Effective dose of Debio0932 giving 90% inhibition |
| 0.86-0.9 | Slight Synergism | ED95 | Effective dose of Debio0932 giving 95% inhibition |
| 0.91-1.10 | Nearly Additive | CIwt | Weighted Combination Index. (CI50 + 2CI75 + 3CI90 + 4CI95)/10 |
| 1.11-1.20 | Slight Antagonism | Dm | Median Effect Dose. The dose that produces 50% effect such as IC50 |
| 1.21-1.45 | Moderate Antagonism | m | The shape parameter for the dose effect curve; m = 1, m > 1 and m < 1 indicate hyperbolic, sigmoidal and flat sigmoidal respectively |
| 1.46-3.3 | Antagonism | r | The conformity parameter for goodness of fit. It is the linear correlation coefficient by the median-effect plot |
| 3.4-10 | Strong Antagonism | | |
| >10 | Very Strong Antagonism | | |

The verbal descriptions of CI in Tables 4 to 7 are based on the CIwt.

BT474 Hormone Sensitive Breast Cancer Cells

When the effect on BT474 cell viability of CBD in combination with phytocannabinoids was tested, the 1:1 combinations with CBG and THCV in cells tested in media containing 1% FBS gave CIwt values that were scored as moderate synergism (Table 4).

All other combinations under these conditions were scored within the antagonism range.

TABLE 4

CI values of CBD:phytocannabinoid combinations in BT474 cells in 1% FBS

| Phytocannabinoid/ combination | CI values | | | | | | | | |
|---|---|---|---|---|---|---|---|---|---|
| | ED50 | ED75 | ED90 | ED95 | CIwt | Dm | m | r | Summary |
| CBD | N/A | N/A | N/A | N/A | N/A | 16.85 | 1.93 | 0.936 | |
| CBG | N/A | N/A | N/A | N/A | N/A | 14.85 | 1.76 | 0.973 | |
| CBGA | N/A | N/A | N/A | N/A | N/A | 27.86 | 2.06 | 0.986 | |
| CBDA | N/A | N/A | N/A | N/A | N/A | 43.27 | 3.20 | 0.993 | |
| THCV | N/A | N/A | N/A | N/A | N/A | 20.27 | 1.93 | 0.947 | |
| CBD:CBG | 0.79 | 0.77 | 0.76 | 0.75 | 0.76 | 6.24 | 1.91 | 0.947 | Moderate synergism |
| CBD:CBGA | 1.18 | 1.36 | 1.59 | 1.77 | 1.57 | 14.36 | 1.71 | 0.970 | Antagonism |
| CBD:CBDA | 1.16 | 1.39 | 1.67 | 1.89 | 1.65 | 12.13 | 1.48 | 0.967 | Antagonism |
| CBD:THCV | 0.75 | 0.75 | 0.76 | 0.76 | 0.76 | 6.88 | 1.91 | 0.948 | Moderate synergism |
| CBD5:CBG1 | 1.35 | 1.34 | 1.34 | 1.34 | 1.34 | 18.46 | 1.90 | 0.944 | Moderate Antagonism |
| CBD5:CBGA1 | 1.18 | 1.22 | 1.26 | 1.29 | 1.26 | 18.43 | 1.89 | 0.942 | Moderate Antagonism |
| CBD5:CBDA1 | 0.43 | 1.05 | 2.56 | 4.69 | 2.90 | 6.47 | 0.75 | 0.910 | Antagonism |
| CBD5:THCV1 | 1.51 | 1.58 | 1.65 | 1.70 | 1.64 | 21.75 | 1.78 | 0.945 | Antagonism |

MDA-MB-231 Breast Cancer Cells

In the MDA-MB-231 cells, the CIwt values generated showed that the effect on cell viability of CBD in combination with phytocannabinoids was scored within the synergism range or nearly additive for all combinations apart from the 1:1 combinations with CBG and CBGA in media containing 1% FBS (Table 5).

TABLE 5

CI values of CBD:phytocannabinoid combinations in MDA-MB-231 cells in 1% FBS

| Phytocannabinoid/ combination | CI values | | | | | | | | |
|---|---|---|---|---|---|---|---|---|---|
| | ED50 | ED75 | ED90 | ED95 | CIwt | Dm | m | r | Summary |
| CBD | N/A | N/A | N/A | N/A | N/A | 5.61 | 0.78 | 0.815 | |
| CBG | N/A | N/A | N/A | N/A | N/A | 14.25 | 2.11 | 0.903 | |
| CBGA | N/A | N/A | N/A | N/A | N/A | 43.53 | 2.10 | 0.897 | |
| CBDA | N/A | N/A | N/A | N/A | N/A | 19.98 | 0.86 | 0.752 | |
| THCV | N/A | N/A | N/A | N/A | N/A | 38.97 | 2.21 | 0.894 | |
| CBD:CBG | 2.32 | 1.55 | 1.26 | 1.20 | 1.40 | 9.32 | 1.64 | 0.947 | Moderate Antagonism |
| CBD:CBGA | 1.77 | 1.34 | 1.17 | 1.18 | 1.27 | 8.78 | 1.12 | 0.776 | Moderate Antagonism |
| CBD:CBDA | 1.02 | 0.89 | 0.79 | 0.72 | 0.80 | 4.46 | 0.88 | 0.900 | Moderate Synergism |
| CBD:THCV | 2.60 | 1.24 | 0.69 | 0.52 | 0.92 | 12.74 | 2.23 | 0.894 | Nearly Additive |
| CBD5:CBG1 | 2.47 | 1.10 | 0.54 | 0.37 | 0.78 | 12.85 | 2.22 | 0.893 | Moderate Synergism |
| CBD5:CBGA1 | 1.04 | 0.92 | 0.85 | 0.85 | 0.89 | 5.68 | 0.88 | 0.767 | Slight Synergism |
| CBD5:CBDA1 | 3.14 | 1.34 | 0.58 | 0.32 | 0.89 | 16.66 | 1.99 | 0.905 | Slight Synergism |
| CBD5:THCV1 | 2.91 | 1.28 | 0.60 | 0.37 | 0.88 | 15.88 | 2.01 | 0.894 | Slight Synergism |

SKBR3 Breast Cancer Cells

When SKBR3 cells were tested with CBD:phytocannabinoid combinations in media containing 1% FBS the greatest combination effect was seen in the cells treated with CBD:THCV combination where the CIwt was scored as synergism (Table 6).

TABLE 6

CI values of CBD:phytocannabinoid combinations in SKBR3 cells in 1% FBS

| Phytocannabinoid/ combination | CI values | | | | | Dm | m | r | Summary |
|---|---|---|---|---|---|---|---|---|---|
| | ED50 | ED75 | ED90 | ED95 | CIwt | | | | |
| CBD | N/A | N/A | N/A | N/A | N/A | 9.31 | 2.64 | 0.895 | |
| CBG | N/A | N/A | N/A | N/A | N/A | 8.55 | 2.51 | 0.930 | |
| CBGA | N/A | N/A | N/A | N/A | N/A | 16.82 | 1.97 | 0.946 | |
| CBDA | N/A | N/A | N/A | N/A | N/A | 30.02 | 2.57 | 0.913 | |
| THCV | N/A | N/A | N/A | N/A | N/A | 18.32 | 1.94 | 0.948 | |
| CBD:CBG | 1.26 | 1.44 | 1.66 | 1.82 | 1.64 | 5.62 | 1.95 | 0.940 | Antagonism |
| CBD:CBGA | 1.68 | 1.63 | 1.58 | 1.55 | 1.59 | 10.09 | 2.55 | 0.910 | Antagonism |
| CBD:CBDA | 1.11 | 1.16 | 1.21 | 1.24 | 1.20 | 7.90 | 2.39 | 0.947 | Slight Antagonism |
| CBD:THCV | 0.62 | 0.61 | 0.61 | 0.61 | 0.61 | 3.84 | 2.44 | 0.934 | Synergism |
| CBD5:CBG1 | 0.91 | 1.06 | 1.23 | 1.36 | 1.22 | 6.96 | 1.92 | 0.945 | Moderate Antagonism |
| CBD5:CBGA1 | 0.80 | 0.92 | 1.06 | 1.17 | 1.05 | 6.66 | 1.92 | 0.949 | Nearly Additive |
| CBD5:CBDA1 | 0.67 | 0.77 | 0.89 | 0.99 | 0.88 | 5.83 | 1.95 | 0.945 | Slight Synergism |
| CBD5:THCV1 | 1.15 | 1.15 | 1.15 | 1.14 | 1.15 | 9.73 | 2.58 | 0.900 | Slight Antagonism |

Discussion

The aim of the study was to examine in vitro the effects of CBD in combination with four phytocannabinoid compounds (CBG, CBGA, CBDA and THCV) on the viability of three breast cancer cell lines, and a liver cancer cell line in order to determine whether the combinations proved significant additive, antagonistic or synergistic using either statistical significance or the Chou-Talalay Method.

The IC50 Values of Phytocannabinoid:

The IC50 values for each single agent phytocannabinoid were generated for each cell line alone and in combination to generate CI data.

In summary the following observations were seen in this study for phytocannabinoid tested as a single agent:

Potency of phytocannabinoid in 10% FBS was lower than 1% which is likely to be due to plasma binding.

In general each single agent had a similar IC50 value across the panel of 6 cell lines regardless of hormone sensitivity of each line (BT474 is hormone sensitive).

In addition, CBD and CBG on their own were more potent than the acid variants CBDA and CBGA across the cell lines tested.

Combination Index Effect of Phytocannabinoids in Presence of CBD:

The Chou and Talalay method uses the Median Effect Principle based on the mass action law in order to calculate the CI of two agents together. The method takes into account both the potency of a particular compound (Dm) and the shape parameter of the curve (m) of each test agent on its own (in this case CBD and phytocannabinoid agents) as well as the Dm and m of the two agents in combination (Chou, 2006).

Because the shape parameter is taken into account it is possible to have lower Dm values of CBD and phytocannabinoid in combination compared to CBD and phytocannabinoid on their own but the calculated CI value is greater than 1 and so the combined effect is classed as antagonism.

The additive, synergism and antagonism effects of CBD in combination with the phytocannabinoids in the panel of breast cancer cell lines in media containing 1% FBS following analysis using the Chou and Talalay method is summarized in Table 7.

TABLE 7

Summary of CIwt scores for each combination in each cell line in media containing 1% FBS.

| Phytocannabinoid combination | Breast | | |
|---|---|---|---|
| | BT474 | MDA-MB-231 | SKBR3 |
| CBD1:CBG1 | Moderate synergism | Moderate Antagonism | Antagonism |
| CBD1:CBGA1 | Antagonism | Moderate Antagonism | Antagonism |
| CBD1:CBDA1 | Antagonism | Moderate Synergism | Slight Antagonism |
| CBD1:THCV1 | Moderate synergism | Nearly Additive | Synergism |
| CBD5:CBG1 | Moderate Antagonism | Moderate Synergism | Moderate Antagonism |
| CBD5:CBGA1 | Moderate Antagonism | Slight Synergism | Nearly Additive |
| CBD5:CBDA1 | Antagonism | Slight Synergism | Slight Synergism |
| CBD5:THCV1 | Antagonism | Slight Synergism | Slight Antagonism |

In summary the following observations were seen in this study for phytocannabinoid tested as a combination:

The CBD combination which appeared to have the greatest effect on synergism across all cell lines was CBD in combination with THCV at a 1:1 ratio. The effects of this combination gave CIwt values that were scored within the synergistic range or nearly additive in all of the breast cancer cell lines BT474, MDA-MB-231, SKBR3.

CBD in combination with CBG at a 1:1 ratio was synergistic in the BT474 cell line.

The cell line where the effect of combinations appeared to have the greatest effect was the MDA-MB-231 line where all of the combinations apart from the CBD:CBG and CBD:CBGA gave CIwt values that scored within the synergism range or were nearly additive.

CBD appears to be most effective either in combination with either THCV or CBG at a 1:1 ratio depending on the cell line. MDA-MB-231 breast cancer cells appear to be most sensitive to the CBD:phytocannabinoid combinations.

EXAMPLE 2

Efficacy of Phytocannabinoids Alone and in Combination in Lung, Pancreatic, Skin, Ovarian, Gastric, Renal and Bladder Cancer Cell Lines Materials and Methods
Cell Lines:

The following cell lines were tested in this example: Lung Cancer (A549, NCI-H460); Pancreatic cancer (PANC1, Mia-Pa-Ca-2); Melanoma (WM115, A375); Ovarian cancer (OVCAR3, SKOV3); Gastric cancer (MKN45, HGC-27); Renal cancer (ACHN) and Bladder Cancer (RT112).

Phytocannabinoid Preparations:

The phytocannabinoids tested were as follows: Cannabidiol (CBD); Cannabidiolic Acid (CBDA); Cannabigerol (CBG); Cannabigerol Acid (CBGA); Tetrahydrocannabivarin (THCV); and Tetrahydrocannabinol (THC).

The positive control agents used were Taxotere (Docetaxel), Cisplatin and Gemcitabine.

Cell Preparation:

Each tumour cell line was maintained in vitro in RPMI 1640+10% heat inactivated FBS and 2 mM L-glutamine (growth media) at 37° C. in 5% $CO_2$ and humidified conditions. The cells were harvested, washed, re-suspended into growth medium and counted. The cells were re-suspended into assay media (RPMI 1640+5% heat inactivated FBS+ and 2 mM L-glutamine) at $4 \times 10^4$ cells/ml (dependent upon cell type) and plated into the middle 240 wells of 384 well tissue culture plates (Corning CellBind, black-wall plates) 25 µl/well aliquots; 50 µl of growth media was aliquoted into the outer wells. There were 3 plates for each cell line.

The plates were incubated overnight at 37° C., in 5% humidified $CO_2$.

Phytocannabinoid Preparation and Plating (1% FBS):

The phytocannabinoid test compounds were prepared in 100% DMSO vehicle at a stock concentration of 20 and 40 mM.

Dilution of Single Cannabinoid Compound on its Own:

Starting with the 20 mM stock in DMSO, this was serially diluted (2 fold) in DMSO in a 96-well plate, to 20 (no dilution), 10, 5, 2.5, 1.25, 0.625, 0.315, 0.157 and 0.79 mM. Following this, 10 ul of each compound dilution was diluted into 990 ul of 1% (v/v) FBS media in a deep well block making the final concentrations of 200, 100, 50, 25, 12.5, 6.25, 3.125, 1.56 and 0.79 µM (2× final assay concentrations and 1% DMSO).

All Compounds in 1:1 Ratio:

An equal volume of each cannabinoid in the combination (stock concentration 40 mM) was mixed together to make a stock of 20 mM of each cannabinoid in DMSO. This was serially diluted (2 fold) in DMSO in a 96-well plate, to 20 (no dilution), 10, 5, 2.5, 1.25, 0.625, 0.315, 0.157 and 0.79 mM. Following this, 10 ul of each combination dilution was diluted into 990 ul of 1% (v/v) FBS media in a deep well block making the final concentrations of 200, 100, 50, 25, 12.5, 6.25, 3.125, 1.56 and 0.79 µM (2× final assay concentrations and 1% DMSO).

Positive Controls

Taxotere SOC was prepared in 100% DMSO to give a stock concentration of 10 mM. This was diluted in DMSO from the stock solution to 200 µM, then serially diluted (3-fold) in DMSO to 200 (no dilution), 66.66, 22.22, 7.41, 2.47, 0.82, 0.27, 0.09, 0.03 µM. 10 ul of each of the taxotere dilutions was diluted in 990 ul of 1% (v/v) FBS media making the final concentrations of 2, 0.67, 0.22, 0.074, 0.0247, 0.0082, 0.0027 0.0009, 0.0003 µM (2× final assay concentrations and 1% DMSO).

Gemcitabine SOC was prepared in 100% DMSO to give a stock concentration of 20 mM. This was then serially diluted (3 fold) in DMSO in a 96-well plate, to 20 (no dilution), 6.6, 2.2, 0.741, 0.247, 0.082, 0.027, 0.009 and 0.003 mM. Following this, 10 ul of each dilution was further diluted into 990 ul of 1% (v/v) FBS media making the final concentrations of 200 (no dilution), 66.66, 22.22, 7.41, 2.47, 0.82, 0.27, 0.09, 0.03 µM (2× final assay concentrations and 1% DMSO).

Cisplatin (stock of 1 mg/ml=3.33 mM in water) was diluted in 1% FBS media to give a stock concentration of 1 mM. This was then diluted in 1% FBS media from the stock solution to 200 µM, then serially diluted (3-fold) in 1% FBS media to 200 (no dilution), 66.66, 22.22, 7.41, 2.47, 0.82, 0.27, 0.09, 0.03 µM (2× final assay concentrations; no DMSO).

Assay Conditions:

The plates were incubated for 72 h at 37° C. in 5% humidified $CO_2$. To develop the plates, at 72 h, 10 µl of CellTiter-Blue™ reagent was added to each test/blank well.

The plates were incubated at 37° C., 5% humidified $CO_2$. Fluorescence was measured using a Flex II Station plate reader (570 nm excitation wavelength, 600 nm emission wavelength, 590 nm cut-off) after 3 h.

Results

The phytocannabinoid compounds CBD, CBGA, CBG, CBDA, THCV and THC were tested on a panel of lung (A549, NCI-H460), pancreatic (PANC1, Mia-Pa-Ca-2), melanoma (WM115, A375), ovarian (OVCAR3, SKOV3), gastric (MKN45, HGC-27), renal (ACHN) and bladder (RT112) cancer cell lines according to the protocol for 72 h in media containing 1% FBS.

The $IC_{50}$ values for each phytocannabinoid and combination of CBD with the other phytocannabinoids was calculated for each cell line. The raw data values expressed in relative fluorescent units were normalised to the vehicle for each individual plate and any reduction in fluorescence indicated a decrease in viability.

Tables 8 and 9 below provide the $IC_{50}$ values for the phytocannabinoids and the combinations of phytocannabinoids.

TABLE 8

$IC_{50}$ values of Phytocannabinoids and CBD:phytocannabinoid combinations in cell lines in the presence of 1% FBS

| | Cell line $IC_{50}$ value (µM) | | | | | |
|---|---|---|---|---|---|---|
| | LUNG | | PANCREATIC | | MELANOMA | |
| | | NCI | | Mia- | | |
| | A549 | H460 | PANC-1 | Pa-Ca-2 | WM115 | A375 |
| CBD | 3.2 | 2.5 | 3.0 | 2.6 | 2.4 | 2.9 |
| CBGA | 6.1 | 6.2 | 8.5 | 8.9 | 1.5 | 7.3 |
| CBG | 4.3 | 4.0 | 3.1 | 2.2 | 3.1 | 2.1 |
| CBDA | 8.5 | 7.3 | 13.1 | 7.9 | 2.1 | 10.2 |
| THCV | 7.4 | 4.6 | 6.5 | 5.2 | 6.5 | 5.0 |
| THC | 5.5 | 3.8 | 3.0 | 2.9 | 2.9 | 2.7 |
| CBD1:CBG1 | 1.6 | 0.8* | 1.2* | 0.8* | 1.0 | 0.9 |
| CBD1:CBGA1 | 2.2 | 1.5 | 2.9 | 2.3 | 2.9 | 2.9 |
| CBD1:CBDA1 | 2.0 | 1.3* | 3.0 | 2.0 | 2.1 | 2.9 |
| CBD1:THCV1 | 1.6 | 1.4* | 1.5 | 1.5* | 1.5 | 1.5 |
| CBD1:THC1 | 1.5 | 1.2* | 1.5 | 1.0* | 1.1 | 1.4 |
| TAXOTERE** | 0.6 | 1.1 | NT | NT | NT | NT |
| CISPLATIN | NT | NT | NT | NT | 35 | 6.3 |
| GEMCITABINE | NT | NT | >100 | >100 | NT | NT |

*= significantly different (p = <0.05) from CBD or other phytocannabinoid on their own
**Measured in nM

TABLE 9

IC$_{50}$ values of Phytocannabinoids and CBD:phytocannabinoid combinations in cell lines in the presence of 1% FBS

| | Cell line IC$_{50}$ value (µM) | | | | | |
|---|---|---|---|---|---|---|
| | OVARIAN | | | GASTRIC | RENAL | BLADDER |
| | OVCAR3 | SKOV3 | MKN45 | HGC-27 | ACHN | RT112 |
| CBD | 2.8 | 3.1 | 3.4 | 1.5 | 3.3 | 2.0 |
| CBGA | 6.1 | 7.9 | 6.5 | 7.8 | 11.6 | 9.8 |
| CBG | 5.3 | 5.5 | 4.3 | 1.6 | 3.0 | 2.5 |
| CBDA | 6.7 | 1.3 | 8.8 | 1.3 | 10.7 | 8.2 |
| THCV | 6.5 | 6.5 | 6.5 | 4.1 | 6.8 | 4.7 |
| THC | 5.9 | 5.3 | 4.2 | 2.8 | 3.6 | 3.6 |
| CBD1:CBG1 | 0.9 | 1.4 | 1.3 | 0.6 | 1.4 | 0.8* |
| CBD1:CBGA1 | 1.9* | 3.0 | 2.6 | 2.4 | 3.0 | 2.4 |
| CBD1:CBDA1 | 1.6* | 2.9 | 2.6 | 2.1 | 3.0 | 2.4 |
| CBD1:THCV1 | 1.6 | 1.5 | 1.7 | 1.5 | 1.5 | 1.4* |
| CBD1:THC1 | 1.4 | 1.7 | 1.7 | 1.4 | 1.3 | 1.4* |
| TAXOTERE** | NT | NT | NT | NT | 1.8 | NT |
| CISPLATIN | 7.7 | 4.5 | 9.7 | 47 | NT | 27 |
| GEMCITABINE | NT | NT | NT | NT | NT | NT |

*= significantly different (p = <0.05) from CBD or other phytocannabinoid on their own
**Measured in nM Generation of Combination Index (CI) Values of CBD in Combination with Other Phytocannabinoids Using the Chou-Talalay Method This calculation was as described in Example 1 above.

A549 (Lung NSCLC) Cells:

When the effect on A549 cell viability of CBD in 1:1 combination with phytocannabinoids was tested in media containing 1% FBS, the combinations with CBG and THCV gave CI$_{wt}$ values that were scored in the synergistic range (Table 10).

The CBD:CBDA and CBD:THC combinations gave a CIwt which scored as nearly additive. The CBD:CBGA combination scored as slightly antagonistic.

TABLE 10

Combination Index values of CBD:phytocannabinoid combinations in A549 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.87 | 5.17 | 0.96 | |
| CBGA | | N/A | N/A | N/A | N/A | N/A | 6.89 | 4.27 | 0.98 | |
| CBG | | N/A | N/A | N/A | N/A | N/A | 4.23 | 10.40 | 1.00 | |
| CBDA | | N/A | N/A | N/A | N/A | N/A | 7.60 | 2.30 | 0.96 | |
| THCV | | N/A | N/A | N/A | N/A | N/A | 6.59 | 4.01 | 0.96 | |
| THC | | N/A | N/A | N/A | N/A | N/A | 4.08 | 13.60 | 1.00 | |
| CBD1 | CBG1 | 0.85 | 0.87 | 0.90 | 0.92 | 0.89 | 1.45 | 5.64 | 0.99 | Slight Synergism |
| CBD1 | CBGA1 | 0.99 | 1.05 | 1.13 | 1.18 | 1.12 | 2.00 | 3.76 | 0.99 | Slight Antagonism |
| CBD1 | CBDA1 | 0.97 | 0.98 | 1.01 | 1.04 | 1.01 | 2.01 | 3.73 | 0.99 | Nearly Additive |
| CBD1 | THCV1 | 0.74 | 0.71 | 0.68 | 0.66 | 0.69 | 1.49 | 5.87 | 1.00 | Synergism |
| CBD1 | THC1 | 0.82 | 0.87 | 0.92 | 0.96 | 0.91 | 1.38 | 5.25 | 0.99 | Nearly Additive |

H460 (Lung NSCLC) Cells

When the effect on H460 cell viability of CBD in 1:1 combination with phytocannabinoids was tested in media containing 1% FBS, all the combinations gave CI$_{wt}$ values that were scored in the synergistic range (Table 11).

TABLE 11

Combination Index values of CBD:phytocannabinoid combinations in NCI-H460 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.55 | 6.24 | 1.00 | |
| CBGA | | N/A | N/A | N/A | N/A | N/A | 4.03 | 2.68 | 0.96 | |
| CBG | | N/A | N/A | N/A | N/A | N/A | 3.96 | 13.62 | 1.00 | |

TABLE 11-continued

Combination Index values of CBD:phytocannabinoid combinations in NCI-H460 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBDA | | N/A | N/A | N/A | N/A | N/A | 6.60 | 3.32 | 0.97 | |
| THCV | | N/A | N/A | N/A | N/A | N/A | 4.53 | 4.47 | 0.99 | |
| THC | | N/A | N/A | N/A | N/A | N/A | 3.28 | 5.34 | 0.95 | |
| CBD1 | CBG1 | 0.50 | 0.53 | 0.57 | 0.60 | 0.57 | 0.77 | 5.32 | 0.99 | Synergism |
| CBD1 | CBGA1 | 0.84 | 0.79 | 0.76 | 0.74 | 0.76 | 1.32 | 5.49 | 1.00 | Moderate Synergism |
| CBD1 | CBDA1 | 0.73 | 0.75 | 0.78 | 0.80 | 0.78 | 1.35 | 4.49 | 1.00 | Moderate Synergism |
| CBD1 | THCV1 | 0.90 | 0.87 | 0.85 | 0.84 | 0.86 | 1.47 | 6.28 | 1.00 | Slight Synergism |
| CBD1 | THC1 | 0.82 | 0.79 | 0.77 | 0.75 | 0.77 | 1.17 | 6.93 | 1.00 | Moderate Synergism |

PANC-1 (Pancreatic Cancer) Cells

When the effect on PANC-1 cell viability of CBD in 1:1 combination with phytocannabinoids was tested in media containing 1% FBS, the combinations with CBG, THCV and THC gave $CI_{wt}$ values that were scored in the synergistic range (Table 12). The CBD:CBGA and CBD:CBDA combinations gave a $CI_{wt}$ which scored as moderate antagonism.

TABLE 12

Combination Index values of CBD:phytocannabinoid combinations in PANC-1 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.92 | 7.80 | 1.00 | |
| CBGA | | N/A | N/A | N/A | N/A | N/A | 8.82 | 4.12 | 1.00 | |
| CBG | | N/A | N/A | N/A | N/A | N/A | 2.88 | 5.52 | 1.00 | |
| CBDA | | N/A | N/A | N/A | N/A | N/A | 12.63 | 3.11 | 1.00 | |
| THCV | | N/A | N/A | N/A | N/A | N/A | 6.46 | 6.63 | 1.00 | |
| THC | | N/A | N/A | N/A | N/A | N/A | 3.15 | 6.63 | 1.00 | |
| CBD1 | CBG1 | 0.84 | 0.87 | 0.90 | 0.92 | 0.90 | 1.21 | 5.31 | 1.00 | Slight Synergism |
| CBD1 | CBGA1 | 1.31 | 1.30 | 1.28 | 1.27 | 1.29 | 2.88 | 7.00 | 0.99 | Moderate Antagonism |
| CBD1 | CBDA1 | 1.32 | 1.30 | 1.30 | 1.30 | 1.30 | 3.12 | 6.50 | 1.00 | Moderate Antagonism |
| CBD1 | THCV1 | 0.73 | 0.76 | 0.78 | 0.80 | 0.78 | 1.47 | 6.16 | 1.00 | Moderate Synergism |
| CBD1 | THC1 | 0.77 | 0.78 | 0.80 | 0.80 | 0.79 | 1.54 | 6.63 | 1.00 | Moderate Synergism |

MIA-PA-CA2 (Pancreatic Cancer) Cells

When the effect on MIA-PA-CA2 cell viability of CBD in 1:1 combination with phytocannabinoids was tested in media containing 1% FBS, the combinations with CBG, CBDA, THCV and THC gave $CI_{wt}$ values that were scored in the synergistic or nearly additive range (Table 13). The CBD:CBGA combination gave a $CI_{wt}$ which scored as moderate antagonism.

TABLE 13

Combination Index values of CBD:phytocannabinoid combinations in MIA-PA-CA2 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.00 | 3.26 | 0.95 | |
| CBGA | | N/A | N/A | N/A | N/A | N/A | 8.67 | 4.65 | 1.00 | |
| CBG | | N/A | N/A | N/A | N/A | N/A | 2.06 | 2.87 | 1.00 | |
| CBDA | | N/A | N/A | N/A | N/A | N/A | 7.09 | 2.03 | 0.99 | |
| THCV | | N/A | N/A | N/A | N/A | N/A | 4.79 | 4.45 | 1.00 | |
| THC | | N/A | N/A | N/A | N/A | N/A | 2.64 | 5.72 | 0.99 | |
| CBD1 | CBG1 | 0.95 | 0.86 | 0.77 | 0.72 | 0.79 | 0.96 | 4.25 | 0.96 | Moderate Synergism |
| CBD1 | CBGA1 | 1.27 | 1.26 | 1.26 | 1.26 | 1.26 | 2.06 | 3.52 | 0.99 | Moderate Antagonism |
| CBD1 | CBDA1 | 1.13 | 1.07 | 1.02 | 1.00 | 1.03 | 1.76 | 3.37 | 0.99 | Nearly Additive |

TABLE 13-continued

Combination Index values of CBD:phytocannabinoid combinations in MIA-PA-CA2 cells in 1% FBS

| | | Combination Index Values | | | | | | | |
|---|---|---|---|---|---|---|---|---|---|
| | | ED50 | ED75 | ED90 | ED95 | CIwt | Dm | m | r | Score |
| CBD1 | THCV1 | 0.92 | 0.83 | 0.74 | 0.69 | 0.76 | 1.30 | 5.48 | 0.98 Moderate Synergism |
| CBD1 | THC1 | 0.94 | 0.85 | 0.77 | 0.72 | 0.78 | 1.07 | 6.67 | 1.00 Moderate Synergism |

WM115 (Melanoma) Cells

When the effect on WM115 cell viability of CBD in 1:1 combination with phytocannabinoids was tested in media containing 1% FBS, all the combinations gave $CI_{wt}$ values that were scored in the synergistic range (Table 14).

TABLE 14

Combination Index values of CBD:phytocannabinoid combinations in WM115 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.77 | 2.11 | 1.00 | |
| CBGA | | N/A | N/A | N/A | N/A | N/A | 12.87 | 3.78 | 0.98 | |
| CBG | | N/A | N/A | N/A | N/A | N/A | 3.10 | 3.25 | 1.00 | |
| CBDA | | N/A | N/A | N/A | N/A | N/A | 14.73 | 3.16 | 0.94 | |
| THCV | | N/A | N/A | N/A | N/A | N/A | 6.43 | 6.56 | 1.00 | |
| THC | | N/A | N/A | N/A | N/A | N/A | 3.17 | 6.44 | 1.00 | |
| CBD1 | CBG1 | 0.73 | 0.64 | 0.56 | 0.52 | 0.58 | 1.07 | 3.69 | 0.99 | Synergism |
| CBD1 | CBGA1 | 1.19 | 0.94 | 0.75 | 0.65 | 0.79 | 2.71 | 4.56 | 0.99 | Moderate Synergism |
| CBD1 | CBDA1 | 0.93 | 0.73 | 0.57 | 0.49 | 0.61 | 2.17 | 4.46 | 1.00 | Synergism |
| CBD1 | THCV1 | 0.76 | 0.61 | 0.50 | 0.45 | 0.53 | 1.47 | 6.13 | 1.00 | Synergism |
| CBD1 | THC1 | 0.72 | 0.63 | 0.57 | 0.54 | 0.59 | 1.06 | 5.16 | 0.99 | Synergism |

A375 (Melanoma) Cells

When the effect on A375 cell viability of CBD in 1:1 combination with phytocannabinoids was tested in media containing 1% FBS, the combinations of CBD with CBG and THCV gave $CI_{wt}$ values that were scored as moderate synergism whereas the other three combinations scored in the antagonism range (Table 15).

TABLE 15

Combination Index values of CBD:phytocannabinoid combinations in A375 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.66 | 8.30 | 1.00 | |
| CBGA | | N/A | N/A | N/A | N/A | N/A | 6.66 | 3.46 | 1.00 | |
| CBG | | N/A | N/A | N/A | N/A | N/A | 1.89 | 3.24 | 0.99 | |
| CBDA | | N/A | N/A | N/A | N/A | N/A | 9.78 | 3.85 | 0.96 | |
| THCV | | N/A | N/A | N/A | N/A | N/A | 5.54 | 5.87 | 1.00 | |
| THC | | N/A | N/A | N/A | N/A | N/A | 2.47 | 4.67 | 0.99 | |
| CBD1 | CBG1 | 0.80 | 0.76 | 0.73 | 0.72 | 0.74 | 0.89 | 5.51 | 1.00 | Moderate synergism |
| CBD1 | CBGA1 | 0.88 | 1.01 | 1.16 | 1.27 | 1.15 | 1.68 | 3.49 | 1.00 | Slight antagonism |
| CBD1 | CBDA1 | 1.28 | 1.24 | 1.21 | 1.19 | 1.22 | 2.68 | 8.30 | 1.00 | Moderate antagonism |
| CBD1 | THCV1 | 0.77 | 0.75 | 0.74 | 0.73 | 0.74 | 1.38 | 8.29 | 1.00 | Moderate synergism |
| CBD1 | THC1 | 1.23 | 1.19 | 1.16 | 1.14 | 1.17 | 1.57 | 7.13 | 0.99 | Slight Antagonism |

OVCAR3 (Ovarian Cancer) Cells

When the effect on OVCAR3 cell viability of CBD in 1:1 combination with phytocannabinoids was tested in media containing 1% FBS, the combinations of CBD with CBG, CBGA, CBDA and THCV gave $CI_{wt}$ values that scored in the synergism range whereas and the combination of CBD with THC scored as nearly additive (Table 16).

TABLE 16

Combination Index values of CBD:phytocannabinoid combinations in OVCAR3 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 2.14 | 3.52 | 0.96 | |
| CBGA | | N/A | N/A | N/A | N/A | N/A | 6.41 | 2.93 | 0.99 | |
| CBG | | N/A | N/A | N/A | N/A | N/A | 4.33 | 12.48 | 1.00 | |
| CBDA | | N/A | N/A | N/A | N/A | N/A | 5.51 | 2.50 | 0.98 | |
| THCV | | N/A | N/A | N/A | N/A | N/A | 6.51 | 6.63 | 1.00 | |
| THC | | N/A | N/A | N/A | N/A | N/A | 4.42 | 13.26 | 1.00 | |
| CBD1 | CBG1 | 0.63 | 0.61 | 0.60 | 0.60 | 0.61 | 0.91 | 5.49 | 1.00 | Synergism |
| CBD1 | CBGA1 | 0.89 | 0.85 | 0.82 | 0.80 | 0.82 | 1.43 | 3.85 | 0.97 | Moderate synergism |
| CBD1 | CBDA1 | 0.92 | 0.85 | 0.80 | 0.76 | 0.81 | 1.42 | 4.02 | 0.99 | Moderate synergism |
| CBD1 | THCV1 | 0.85 | 0.82 | 0.80 | 0.78 | 0.80 | 1.36 | 4.56 | 0.98 | Moderate synergism |
| CBD1 | THC1 | 0.91 | 0.90 | 0.90 | 0.91 | 0.91 | 1.32 | 4.99 | 0.99 | Nearly additive |

SKOV3 (Ovarian Cancer) Cells

When the effect on SKOV3 cell viability of CBD in 1:1 combination with phytocannabinoids was tested in media containing 1% FBS, the combinations of CBD with CBG and THCV gave $CI_{wt}$ values that were scored as synergism. The combinations of CBD with CBDA and THC gave $CI_{wt}$ values that scored as nearly additive whereas and the combination of CBD with CBGA scored as slight antagonism (Table 17).

TABLE 17

Combination Index values of CBD:phytocannabinoid combinations in SKOV3 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 3.17 | 6.45 | 1.00 | |
| CBGA | | N/A | N/A | N/A | N/A | N/A | 8.64 | 4.58 | 1.00 | |
| CBG | | N/A | N/A | N/A | N/A | N/A | 4.75 | 8.30 | 0.95 | |
| CBDA | | N/A | N/A | N/A | N/A | N/A | 10.57 | 2.76 | 0.99 | |
| THCV | | N/A | N/A | N/A | N/A | N/A | 6.58 | 6.50 | 1.00 | |
| THC | | N/A | N/A | N/A | N/A | N/A | 4.56 | 12.17 | 1.00 | |
| CBD1 | CBG1 | 0.70 | 0.68 | 0.67 | 0.66 | 0.67 | 1.33 | 8.30 | 1.00 | Synergism |
| CBD1 | CBGA1 | 1.20 | 1.15 | 1.11 | 1.08 | 1.11 | 2.79 | 7.50 | 1.00 | Slight antagonism |
| CBD1 | CBDA1 | 1.14 | 1.06 | 0.99 | 0.96 | 1.01 | 2.78 | 7.50 | 1.00 | Nearly Additive |
| CBD1 | THCV1 | 0.66 | 0.65 | 0.64 | 0.63 | 0.64 | 1.41 | 7.16 | 1.00 | Synergism |
| CBD1 | THC1 | 0.96 | 0.93 | 0.89 | 0.87 | 0.90 | 1.80 | 11.28 | 1.00 | Slight Synergism |

MKN45 (Gastric Cancer) Cells

When the effect on MKN45 cell viability of CBD in 1:1 combination with phytocannabinoids was tested in media containing 1% FBS, the combinations of CBD with CBG, THCV and THC gave $CI_{wt}$ values that were scored in the synergism range. The combinations of CBD with CBGA and CBDA gave $CI_{wt}$ values that scored as nearly additive (Table 18).

TABLE 18

Combination Index values of CBD:phytocannabinoid combinations in MKN45 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 3.91 | 9.82 | 1.00 | |
| CBGA | | N/A | N/A | N/A | N/A | N/A | 6.40 | 3.48 | 0.98 | |
| CBG | | N/A | N/A | N/A | N/A | N/A | 4.16 | 10.80 | 1.00 | |
| CBDA | | N/A | N/A | N/A | N/A | N/A | 8.04 | 2.98 | 0.97 | |
| THCV | | N/A | N/A | N/A | N/A | N/A | 6.88 | 5.90 | 1.00 | |

TABLE 18-continued

Combination Index values of CBD:phytocannabinoid combinations in MKN45 cells in 1% FBS

| | | Combination Index Values | | | | | | | |
|---|---|---|---|---|---|---|---|---|---|
| | | ED50 | ED75 | ED90 | ED95 | CIwt | Dm | m | r | Score |
| THC | | N/A | N/A | N/A | N/A | N/A | 4.42 | 13.26 | 1.00 | |
| CBD1 | CBG1 | 0.62 | 0.69 | 0.78 | 0.85 | 0.77 | 1.24 | 4.88 | 1.00 | Moderate synergism |
| CBD1 | CBGA1 | 1.11 | 1.06 | 1.01 | 0.99 | 1.02 | 2.69 | 8.11 | 1.00 | Nearly additive |
| CBD1 | CBDA1 | 1.05 | 1.05 | 1.07 | 1.08 | 1.07 | 2.77 | 5.80 | 1.00 | Nearly additive |
| CBD1 | THCV1 | 0.61 | 0.64 | 0.67 | 0.70 | 0.67 | 1.53 | 5.99 | 0.99 | Synergism |
| CBD1 | THC1 | 0.72 | 0.79 | 0.87 | 0.93 | 0.86 | 1.50 | 5.75 | 0.99 | Slight synergism |

HGC27 (Gastric Cancer) Cells

When the effect on HGC27 cell viability of CBD in 1:1 combination with phytocannabinoids was tested in media containing 1% FBS, the combinations of CBD with CBG, THCV and THC gave $CI_{wt}$ values that were scored as nearly additive. The combinations of CBD with CBGA and CBDA gave $CI_{wt}$ values that scored as antagonism (Table 19).

TABLE 19

Combination Index values of CBD:phytocannabinoid combinations in HGC27 cells in 1% FBS

| | | Combination Index Values | | | | | | | |
|---|---|---|---|---|---|---|---|---|---|
| | | ED50 | ED75 | ED90 | ED95 | CIwt | Dm | m | r | Score |
| CBD | | N/A | N/A | N/A | N/A | N/A | 1.72 | 4.61 | 0.99 | |
| CBGA | | N/A | N/A | N/A | N/A | N/A | 5.47 | 2.41 | 0.96 | |
| CBG | | N/A | N/A | N/A | N/A | N/A | 1.73 | 4.77 | 0.99 | |
| CBDA | | N/A | N/A | N/A | N/A | N/A | 10.39 | 3.86 | 0.99 | |
| THCV | | N/A | N/A | N/A | N/A | N/A | 3.06 | 1.60 | 0.97 | |
| THC | | N/A | N/A | N/A | N/A | N/A | 2.74 | 6.12 | 1.00 | |
| CBD1 | CBG1 | 0.81 | 0.91 | 1.02 | 1.10 | 1.01 | 0.70 | 3.15 | 1.00 | Nearly Additive |
| CBD1 | CBGA1 | 2.19 | 1.96 | 1.76 | 1.65 | 1.80 | 2.87 | 6.33 | 0.96 | Antagonism |
| CBD1 | CBDA1 | 1.90 | 1.77 | 1.65 | 1.57 | 1.67 | 2.80 | 6.33 | 0.94 | Antagonism |
| CBD1 | THCV1 | 1.12 | 1.00 | 0.89 | 0.83 | 0.91 | 1.19 | 10.96 | 1.00 | Nearly Additive |
| CBD1 | THC1 | 1.42 | 1.16 | 0.99 | 0.90 | 1.03 | 1.57 | 6.20 | 0.99 | Nearly Additive |

ACHN (Renal Cancer) Cells

When the effect on ACHN cell viability of CBD in 1:1 combination with phytocannabinoids was tested in media containing 1% FBS, the combinations of CBD with THCV and THC gave $CI_{wt}$ values that scored as synergism and slight synergism respectively. The combinations of CBD with CBG and CBGA gave $CI_{wt}$ values that were scored as nearly additive. The combination of CBD with CBDA scored as moderate antagonism (Table 20).

TABLE 20

Combination Index values of CBD:phytocannabinoid combinations in ACHN cells in 1% FBS

| | | Combination Index Values | | | | | | | |
|---|---|---|---|---|---|---|---|---|---|
| | | ED50 | ED75 | ED90 | ED95 | CIwt | Dm | m | r | Score |
| CBD | | N/A | N/A | N/A | N/A | N/A | 3.11 | 9.47 | 1.00 | |
| CBGA | | N/A | N/A | N/A | N/A | N/A | 12.01 | 6.02 | 0.96 | |
| CBG | | N/A | N/A | N/A | N/A | N/A | 2.96 | 7.00 | 1.00 | |
| CBDA | | N/A | N/A | N/A | N/A | N/A | 8.44 | 3.57 | 0.97 | |
| THCV | | N/A | N/A | N/A | N/A | N/A | 6.76 | 6.63 | 0.98 | |
| THC | | N/A | N/A | N/A | N/A | N/A | 4.40 | 13.12 | 1.00 | |
| CBD1 | CBG1 | 0.96 | 0.97 | 0.99 | 1.00 | 0.99 | 1.45 | 7.13 | 1.00 | Nearly Additive |
| CBD1 | CBGA1 | 1.07 | 1.07 | 1.07 | 1.08 | 1.07 | 2.63 | 8.30 | 1.00 | Nearly Additive |
| CBD1 | CBDA1 | 1.34 | 1.34 | 1.35 | 1.36 | 1.35 | 3.04 | 6.63 | 1.00 | Moderate antagonism |
| CBD1 | THCV1 | 0.65 | 0.65 | 0.65 | 0.65 | 0.65 | 1.38 | 8.29 | 1.00 | Synergism |
| CBD1 | THC1 | 0.72 | 0.80 | 0.89 | 0.96 | 0.88 | 1.31 | 5.22 | 1.00 | Slight Synergism |

RT112 (Bladder Cancer) Cells

When the effect on RT112 cell viability of CBD in 1:1 combination with phytocannabinoids was tested in media containing 1% FBS, the combination of CBD with CBG gave a $CI_{wt}$ value that scored as moderate synergism. The combinations of CBD with THCV and THC gave $CI_{wt}$ values that were scored as nearly additive. The combinations of CBD with CBDA and CBDA gave $CI_{wt}$ values scored as moderate antagonism (Table 21).

TABLE 21

Combination Index values of CBD:phytocannabinoid combinations in RT112 cells in 1% FBS

| | | Combination Index Values | | | | | | | | |
|---|---|---|---|---|---|---|---|---|---|---|
| | | ED50 | ED75 | ED90 | ED95 | CIwt | Dm | m | r | Score |
| CBD | | N/A | N/A | N/A | N/A | N/A | 1.79 | 3.66 | 0.98 | |
| CBGA | | N/A | N/A | N/A | N/A | N/A | 9.72 | 7.33 | 1.00 | |
| CBG | | N/A | N/A | N/A | N/A | N/A | 2.14 | 3.73 | 0.97 | |
| CBDA | | N/A | N/A | N/A | N/A | N/A | 6.36 | 2.11 | 0.98 | |
| THCV | | N/A | N/A | N/A | N/A | N/A | 4.75 | 4.81 | 1.00 | |
| THC | | N/A | N/A | N/A | N/A | N/A | 3.09 | 5.57 | 0.96 | |
| CBD1 | CBG1 | 0.83 | 0.77 | 0.71 | 0.67 | 0.72 | 0.81 | 5.12 | 1.00 | Moderate Synergism |
| CBD1 | CBGA1 | 1.54 | 1.48 | 1.43 | 1.39 | 1.43 | 2.33 | 4.67 | 1.00 | Moderate antagonism |
| CBD1 | CBDA1 | 1.53 | 1.44 | 1.37 | 1.32 | 1.38 | 2.14 | 3.86 | 0.99 | Moderate antagonism |
| CBD1 | THCV1 | 1.04 | 0.96 | 0.89 | 0.85 | 0.90 | 1.35 | 5.42 | 1.00 | Slight synergism |
| CBD1 | THC1 | 1.21 | 1.14 | 1.08 | 1.03 | 1.09 | 1.38 | 5.50 | 1.00 | Nearly Additive |

Discussion

The aim of this Example was to examine in vitro the effects of phytocannabinoids as single agents and also in combination with CBD on the viability of a number of different cancer cell lines in order to determine whether the combinations proved additive, antagonistic or synergistic using the Chou and Talalay method.

Effect of CBD:Phytocannabinoid Combinations

The Chou and Talalay method uses the Median Effect Principle based on the mass action law to calculate the CI of two agents together. The method takes into account both the potency of a particular compound (Dm) and the shape parameter of the curve (m) of each test agent on its own as well as the Dm and m of the agents in combination. The Chou and Talalay Combination Index data for each cell line are in Tables 13 to 24. The weighted combination Index summary scores have been summarized in Table 22.

TABLE 22

Combination Index Summaries of CBD:phytocannabinoid combinations in cell lines

| | Combination | | | | |
|---|---|---|---|---|---|
| Cell Line | CBD1:CBG1 | CBD1:CBGA1 | CBD1:CBDA1 | CBD1:THCV1 | CBD1:THC1 |
| A549 (Lung) | Slight Synergism | Slight Antagonism | Nearly Additive | Synergism | Nearly Additive |
| H460 (Lung) | Synergism | Moderate Synergism | Moderate Synergism | Slight Synergism | Moderate Synergism |
| PANC-1 (Pancreatic) | Slight Synergism | Moderate Antagonism | Moderate Antagonism | Moderate Synergism | Moderate Synergism |
| MIA-PA-CA2 (Pancreatic) | Moderate Synergism | Moderate Antagonism | Nearly Additive | Moderate Synergism | Moderate Synergism |
| WM115 (Melanoma) | Synergism | Moderate Synergism | Synergism | Synergism | Synergism |
| A375 (Melanoma) | Moderate Synergism | Slight Antagonism | Moderate Antagonism | Moderate Synergism | Slight Antagonism |
| OVCAR3 (Ovarian) | Synergism | Moderate Synergism | Moderate Synergism | Moderate Synergism | Nearly Additive |
| SKOV3 (Ovarian) | Synergism | Slight Antagonism | Nearly Additive | Synergism | Nearly Additive |
| MKN45 (Gastric) | Moderate Synergism | Nearly Additive | Nearly Additive | Synergism | Slight Synergism |

TABLE 22-continued

Combination Index Summaries of CBD:phytocannabinoid combinations in cell lines

| Cell Line | CBD1:CBG1 | CBD1:CBGA1 | CBD1:CBDA1 | CBD1:THCV1 | CBD1:THC1 |
|---|---|---|---|---|---|
| HGC27 (Gastric) | Nearly Additive | Antagonism | Antagonism | Nearly Additive | Nearly Additive |
| ACHN (Renal) | Nearly Additive | Nearly Additive | Moderate Antagonism | Synergism | Slight Synergism |
| RT112 (Bladder) | Moderate Synergism | Moderate Antagonism | Moderate Antagonism | Slight Synergism | Nearly Additive |

In summary the following observations using the Chou and Talalay method were seen in this study for CBD:phytocannabinoids tested in combinations:

The cell lines which are most susceptible to the CBD:phytocannabinoid combinations are Lung H460 and Melanoma WM115; where every CBD:phytocannabinoid combination scored in the synergistic range.

The CBD:phytocannabinoid combinations that scored in the synergistic or nearly additive range across all cell lines were CBD1:CBG1 and CBD1:THCV1.

The combination which was least effective and scored in the antagonistic range 7 of the cell lines was CBD1:CBGA1 which was closely followed CBD1:CDBA1 which scored in the antagonistic range across 5 cell lines.

This study shows that the phytocannabinoid compounds under the conditions tested have a clear cytotoxic effect on many different types of cancer cell lines cells and provides potency data similar to Example 1 in which breast, prostate and liver cell lines were tested.

Overall this study demonstrated that when CBD is combined with other phytocannabinoids they have the potential to act synergistically on the viability of a number of different cancer types.

REFERENCES

Baek et al. (1996) Archives of Pharmacol Research, vol 19, No. 3, 1996, pages 228-230 "Synthesis and anti-tumour activity of cannabigerol"

Choi et al. (2008) Biomolecules & Therapeutics, vol 16, 2008, pages 87-94 "Cannabidiol induces cytotoxicity and cell death via apoptotic pathway in cancer cell lines"

Chou T.-C. & Talalay P. Adv. Enzyme Regul. 22:27-55 (1984)

Chou T.-C. Pharmacol. Rev. 58:621-681 (2006)

Ligresti et al. JPET 318:1375-1387 (2006)

McAllister S D, Christian R T, Horowitz M P, Garcia A, Desprez P Y. Mol Cancer Ther. (2007) Nov.; 6(11):2921-7.

The invention claimed is:

1. A method of treating melanoma comprising administering to a patient in need thereof an active pharmaceutical ingredient (API) comprising or consisting essentially of cannabidiol (CBD) and cannabigerol (CBG).

2. The method as claimed in claim 1, wherein the CBD and CBG are present in a ratio of from 7.5:1 to 1:7.5 (CBD:CBG).

3. The method as claimed in claim 2, wherein the CBD and CBG are present in a ratio of 7.5:1 to 2.5:1 (CBD:CBG).

4. The method as claimed in claim 2, wherein the CBD and CBG are present in a ratio of about 5:1 (CBD:CBG).

5. The method as claimed in claim 2, wherein the CBD and CBG are present in a ratio of 2:1 to 1:2 (CBD:CBG).

6. The method as claimed in claim 2, wherein the CBD and CBG are present in a ratio of about 1:1 (CBD:CBG).

7. The method as claimed in claim 1, wherein a dose of the API administered to the subject is between 1 and 1000 mg/kg day.

8. The method as claimed in claim 1, wherein the API is administered as a pharmaceutical formulation comprising the API and one or more excipients.

9. The method as claimed in claim 8, wherein the CBD is formulated for administration separately, sequentially or simultaneously with the CBG or the CBD and CBG are provided in a single dosage form.

* * * * *